US008071782B2

(12) United States Patent
Deng et al.

(10) Patent No.: US 8,071,782 B2
(45) Date of Patent: Dec. 6, 2011

(54) SYNTHESIS OF 1,3,4-TRISUBSTITUTED AND 1,3,4,5-TETRASUBSTITUTED PYRAZOLES

(75) Inventors: Xiaohu Deng, San Diego, CA (US); Neelakandha S. Mani, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 550 days.

(21) Appl. No.: 12/244,184

(22) Filed: Oct. 2, 2008

(65) Prior Publication Data
US 2009/0093637 A1    Apr. 9, 2009

Related U.S. Application Data

(60) Provisional application No. 60/976,907, filed on Oct. 2, 2007.

(51) Int. Cl.
  *C07D 401/02*    (2006.01)
  *C07D 231/56*    (2006.01)
  *C07D 231/10*    (2006.01)
(52) U.S. Cl. .............. 546/275.4; 548/360.1; 548/364.4; 548/375.1; 548/365.7; 548/376.1; 548/377.1
(58) Field of Classification Search ............... 546/275.4; 548/360.1, 364.4, 375.1, 365.7, 376.1, 377.1
See application file for complete search history.

(56) References Cited

OTHER PUBLICATIONS

Abdallah et al "Synthesis and Rearrangement of Pyrazolylamino Alcohols" J Chem Res Syn 1994 vol. 2 pp. 76-77.
Aggarwal et al "A Novel One-Pot Method for the Preparation of Pyrazoles by 1,3-Dipolar Cycloadditions of Diazo Compounds Generated in Situ" J Org Chem 2003 vol. 68 pp. 5381-5383.
Arrieta et al "Efficient Tautomerization Hydrazone-Azomethine Imine Under Microwave Irradiation. Synthesis of [4,3'] and [5,3'] Bipyrazoles" Tetrahedron 1998 vol. 54 pp. 13167-1318.
Bekhit et al "Design, Synthesis and Biological Evaluation of Some Pyrazole Derivatives As Anti-Inflammatory-Anitmicrobial Agents" Bioorg Med Chem 2004 vol. 12 pp. 1935-1945.
Buckingham J "The Chemistry of Arylhydrazones" Q Rev Chem Soc 1969 vol. 23 pp. 37-56.
Carey F A and R J Sundberg "Advanced Organic Chemistry" 3RD ED 1990 Part B p. 21 Plenum Press New York and London.
Daou et al "Regiospecificity of Cycloaddition of Diarylnitrilimines on Some Indole Derivatives" J Heterocycl Chem 1989 26 1485-1488.
Dawood et al "Electolytic Partial Fluorination of Organic Compounds 79. Anodic Fluorination of Spiropyrazoline-5,3'-Chroman-4-Ones and Thiochromanone Analogues. A Route to Aroyl Fluoride Derivative" J Org Chem 2005 vol. 70 pp. 7537-7541.
De Paulis et al "Substituent Effects of N-(1,3-Diphenyl-1-H Pyrazol-5-Yl)Benzamides on Positive Allosteric Modulation of the Metabotropic Glutamate-5 Receptor in Rat Cortical Astrocytes" J Med Chem 2006 vol. 49 pp. 3332-3344.
Del Valle et al "A Short Synthesis of C-Glycosyl Pyrazoles and Pyrroles" J Heterocycl Chem 1995 vol. 32 pp. 899-901.
Deng et al "Reaction of N-Monosubstituted Hydrazones With Nitroolefins: A Novel Regioselective Pyrazole Synthesis" Org Lett 2006 vol. 8 pp. 3505-3508.
Elguero J Comp Heterocycl Chem 1984 5 167.
Elguero J Comp Heterocycl Chem II 1996 3 1-75 and 817-932.
Elguero J et al Targets in Heterocyclic Systems 2002 6 52-98.
Enders et al "Formaldehyde Samp-Hydrazone As a Neutral Chiral Formyl Anion and Cyanide Equivalent Asymmetric Michael Additions to Nitroalkenes" Synthesis 1996 vol. 48-pp. 48-52.
Fathi et al "Regiochemistry of the Cycloadditions of Diphenylnitrilimine to Coumarin, 3-Ethoxycarbonyl and A 3-Acetyl Coumarins. A Reinvestigation" Tetrahedron 1988 Volume pp. 44 4527-4536.
Fernandez et al "Asymmetric Synthesis of Funtionalized Nitrocompounds Through Michael Addition of Formaldehyde Samp Hydrazone to Nitroolefins" Tetrahedron Lett 1994 35 471-472.
Huisgen R "1,3-Dipolar Cycloadditions Past and Future" Angewandte Chem Intl Ed Engl 1963 vol. 2 pp. 565-632.
Kiraet Al "The Vilsmeier-Haack Reaction—III Cyclization of Hydrazones to Pyrazoles" Tetrahedron Lett 1969 vol. 2 pp. 109-110.
Knorr L Ber 1883 vol. 16 pp. 2587 HTTP://WWW.LOOKCHEM.COM/CHEMPEDIA/BASIC-CHEMICAL/CHEMICAL-REACTION/8409.HTML. Accessed Apr. 7, 2011.
Liu et al "Reaction of Aroyl-Substituted Heterocyclic Ketene Aminals With Nitrile !Mines: An Efficient Synthesis of Fully Substituted Pyrazoles and Evidence of Nucleophilic Additional of Enamines to 1,3-Dipoles" Tetrahedron Lett 1999 vol. 40 pp. 7399-7402.
Lokanatha Rai et al "Chloramine-T in Heterocyclic Synthesis; 1 A Simple Procedure for the Generation of Nitrilimines and Its Application to the Synthesis of Pyrazolines" Synth Commun 1989 vol. 19 pp. 2799-2807.
Makino et al "Synthesis of Pyrazoles" J Heterocyl Chem 1998 vol. 35 pp. 489-497.
Mancera et al "Stereoselective Syntheses of Nitropyrazolines by 1,3-Dipolar Cycloaddition of Diazoalkanes to Sugar Nitro Oelfins" J Org Chem 1988 vol. 53 pp. 5648-5651.
Meanwell et al "Structure Activity Relationship Associated With 3,4,5-Triphenyl-1H-Pyrazole-1-Nonanoic Acid, A Nonprostanoid Prostacyclin Mimetic" J Med Chem 1992 vol. 35 pp. 389-397.
Molteni et al "Arylazide Cycloaddition to Methyl Propiolate: DFT-Based Quantitative Prediction of Regioselectivity" Chem Eur J 2003 vol. 9 pp. 2770-2774.
Muthusubramanian et al "Synthesis of Bromonaphtho-pyranoisoxazoles and Pyrazoles As Potential Antimicrobial Agents" Eur J Med Chem—Chim Ther 1986 vol. 21 pp. 163-166.
Padwa A 13-Dipolar Cycloaddition Chemistry John Wiley & Sons: New York 1984 vol. I.
Padwa A Pearson W H Eds Synthetic Applications of 13-Dipolar Cycloaddition Chemistry Toward Heterocycles and Natural Products John Wiley & Sons: New York 2002.
Parham et al "Reaction of Diazo Compounds With Nitroolefins. I. The Preparation of Pyrazoles" J Am Chem Soc 1950 vol. 72 pp. 3843-3846.

(Continued)

*Primary Examiner* — Rebecca Anderson
*Assistant Examiner* — Samantha Shterengarts
(74) *Attorney, Agent, or Firm* — Michael J. Atkins

(57) ABSTRACT

This invention concerns the synthesis of highly substituted pyrazoles, which are structural components of pharmacological compounds, through reaction of hydrazones with nitroolefins.

9 Claims, No Drawings

OTHER PUBLICATIONS

Patel et al "Synthesis of 4,5-Diaryl-1-H-Pyrazole-3-OL-Derivatives As Posential COX-2 Inhibitors" J Org Chem 2004 vol. 69 pp. 7058-7065.

Peruncheralathan et al "Regioselective Synthesis of 1-Aryl-3,4-Substituted/Annulated-5-(Methylthio)Pyrazoles and 1-Aryl-3-(Methyltio)-4-5-Substituted/Annulated Pyrazoles" J Org Chem 2005 vol. 70 pp. 10030-10035.

Press et al "Heterocyclic-Fused Benzopyrans As Cannabinoid Analogues" J Heterocycl Chem 1985 vol. 22 pp. 561-564.

Robertson et al "A Study of Periselectivity in the Thermal Cyclisation Reactions of Diene-Conjugated Diazo Compounds: 1,7-Cyclisation As a Route to 3H-1,2-Diazepines and 1,5 Cyclisation Leading to New Rearrangement Reactions of 3H Pyrazoles" Tetrahedron 1984 vol. 40 pp. 3095-3112.

Singer et al "Alternative Biarylphosphines for Use in the Palladium-Catalyzed Amination of Aryl Halides" Synthesis 2003 vol. 11 pp. 1727-1731.

Singer et al "Development of Nonproprietary Phosphine Ligands for the PD-Catalyzed Amination Reaction" Tetrahedron Lett 2006 vol. 47 pp. 3727-3731.

Singh et al "Synthesis and Characterization of Some Novel Indeno[1,2-C]Pyrazoles" J Chem Res 2005 vol. 8 pp. 526-529).

Stauffer et al "Estrogen Pyrazoles: Defining the Pyrazole Core Structure and the Orientation of Substituents in the Ligand Binding Pocket of the Estrogen Receptor" Bioorg Med Chem 2001 vol. 9 pp. 141-150.

Stott et al "One—Dimensional Noe Experiments Using Pulsed Field Gradients" Magn Reson 1997 vol. 125 pp. 302-324.

Subramanian et al "Synthesis of Naphthopyranoisoxazoles and Naphthopyranopyrazoles Via Cyanoethylation" Synthesis 1984 vol. 12 pp. 1063-1065.

Wang et al Regioselective Synthesis of Unsymmetrical 3,5-Dialkyl-1-Arypyrazoles Org Lett 2000 vol. 2 pp. 3107-3109.

SYNTHESIS OF 1,3,4-TRISUBSTITUTED AND 1,3,4,5-TETRASUBSTITUTED PYRAZOLES

This application claims the benefit of U.S. provisional patent application Ser. No. 60/976,907, filed on Oct. 2, 2007, which is incorporated herein by reference.

FIELD OF THE INVENTION

The present invention relates to methods for the regioselective synthesis of highly substituted pyrazoles from hydrazones and nitroolefins.

BACKGROUND OF THE INVENTION

Pyrazoles are an important class of compounds in the pharmaceutical industry. Compounds containing the pyrazole motif are being developed for a wide range of therapeutic areas including CNS, metabolic diseases and endocrine functions and oncology (Elguero, J. et al. *Targets in Heterocyclic Systems* 2002, 6, 52-98 and reference cited therein). Several pyrazoles have been successfully commercialized, such as the blockbuster drugs sildenafil, celecoxib, and rimonabant:

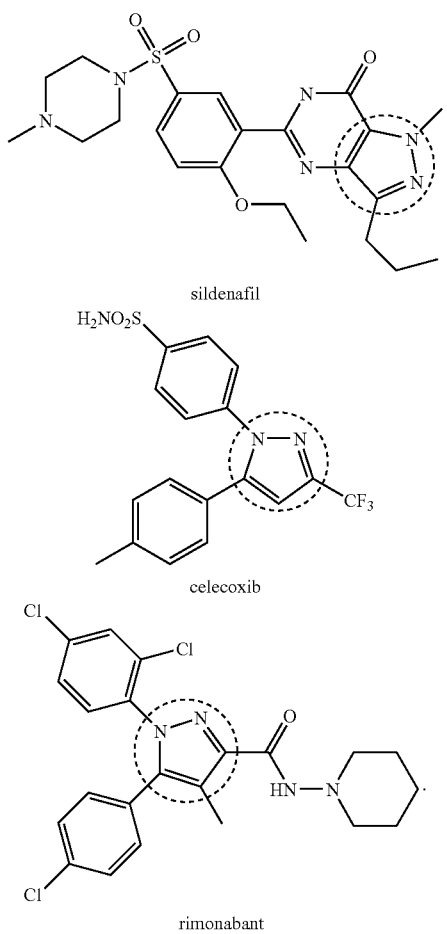

Substituted pyrazoles have also been applied as novel ligands for transition metal-catalyzed cross-coupling reactions ((a) Singer, R. A. et al. *Synthesis* 2003, 1727-1732; (b) Singer, R. A. et al. *Tetrahedron Lett.* 2006, 47, 3727-3731). The synthesis of multi-substituted pyrazoles has been extensively studied, and two methods have certainly stood out in terms of generality and convenience ((a) Elguero, *J. Comp. Heterocycl. Chem.* 1984, 5, 167; (b) Elguero, *J. Comp. Heterocycl. Chem. II* 1996, 3, 1-75, 817-932; (c) Makino, K. et al. *J. Heterocyl. Chem.* 1998, 35, 489-497). One is the venerable Knorr reaction involving the condensation of substituted hydrazines with 1,3-diketones or their derivatives (Scheme 1A) ((a) Knorr, L. *Ber.* 1883, 16, 2587; (b) Patel, M. V. et al. *J. Org. Chem.* 2004, 69, 7058-7065; (c) Peruncheralathan, S. et al. *J. Org. Chem.* 2005, 70, 10030-10035).

Scheme 1A. General methods for pyrazole synthesis.

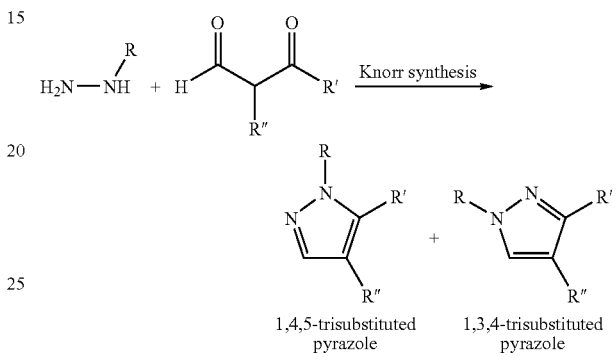

The other method is the 1,3-dipolar cycloaddition of diazoalkanes or nitrile imines with olefins or alkynes (Scheme 1B) ((a) Huisgen, R. *Angew. Chem., Int. Ed. Engl.* 1963, 2, 565-632; (b) Padwa, A. 1,3-*Dipolar Cycloaddition Chemistry*; John Wiley & Sons: New York, 1984; Vol. I; (c) Padwa, A.; Pearson, W. H.; Eds. *Synthetic Applications of* 1,3-*Dipolar Cycloaddition Chemistry Toward Heterocycles and Natural Products*; John Wiley & Sons: New York, 2002).

Scheme 1B. General methods for pyrazole synthesis.

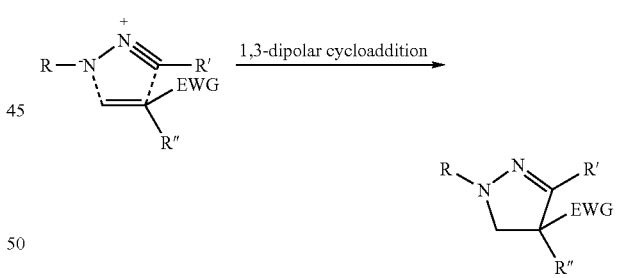

As successful as these two methods are in preparing pyrazoles with various substitution patterns, they are not particularly suited for the regioselective synthesis of 1,3,4-trisubstituted pyrazoles. 1,3,4-Trisubstituted pyrazoles are pharmaceutically important, yet less represented in the literature, probably due to synthetic difficulties ((a) Kira, M. A. et al. *Tetrahedron Lett.* 1969, 2, 109-110; (b) Stauffer, S. R. et al. *Bioorg. Med. Chem.* 2001, 9, 141-150; (c) Bekhit, A. A. et al. *Bioorg. Med. Chem.* 2004, 12, 1935-1945; (d) De Paulis, T. et al. *J. Med. Chem.* 2006, 49, 3332-3344). In the Knorr reaction, the condensation of substituted hydrazines with β-ketoaldehydes usually favors 1,4,5-trisubstituted pyrazoles ((a) Robertson, I. R. et al. *Tetrahedron* 1984, 40, 3095-3112; (b) Subramanian, L. M. et al. *Synthesis* 1984, 12, 1063-1065; (c)

Press, J. B. et al. *J. Heterocycl. Chem.* 1985, 22, 561-4; (d) Muthusubramanian, L. et al. *Eur. J. Med. Chem.* 1986, 21, 163-166; (e) Singh, K. et al. *J. Chem. Res.* 2005, 8, 526-529). One solution to this issue is to prepare a 3,4-disubstituted pyrazole with hydrazine and then introduce the N-1 substituent, but this method is often not regioselective ((a) Meanwell, N. A. et al. *J. Med. Chem.* 1992, 35, 389-397; (b) Wang, X. et al. *Org. Lett.* 2000, 2, 3107-3109; (c) Patel, M. V. et al., 2004).

On the other hand, 1,3-dipolar cycloaddition reactions have been successfully employed to synthesize 1,3,4-trisubstituted pyrazoles, usually regioselectively ((a) Fathi, T. et al. *Tetrahedron* 1988, 44, 4527-4536; (b) Daou, B. et al. *J. Heterocycl. Chem.* 1989, 26, 1485-1488; (c) Lokanatha Rai, K. M. et al. *Synth. Commun.* 1989, 19, 2799-2807; (d) Abdallah, M. A. et al. *J. Chem. Res. Syn.* 1994, 2, 76-77; (e) Del Valle, J. L. et al. *J. Heterocycl. Chem.* 1995, 32, 899; (f) Liu, B. et al. *Tetrahedron Lett.* 1999, 40, 7399; (g) Molteni, G. et al. *Chem. Eur. J.* 2003, 9, 2770; (h) Dawood, K. M.; et al. *J. Org. Chem.* 2005, 70, 7537-7541). However, the difficulty generating and handling the reactive 1,3-dipoles often limits their synthetic utility. Furthermore, an additional oxidation step is often required to transform the pyrazolidine adduct to the pyrazole product.

Recently, a regioselective synthesis of 1,3,5-trisubstituted pyrazoles through reactions of hydrazones with nitroolefins under either neutral (heating in methanol (MeOH) or ethylene glycol) or acidic conditions (trifluoroacetic acid (TFA) in $CF_3CH_2OH$) was reported (Scheme 2, reaction A) (Deng, X.; Mani, N. S. *Org. Lett.* 2006, 8, 3505-3508). Excellent 1,3,5-regioselectivity was achieved, presumably because the aniline nitrogen atom of the hydrazone is more nucleophilic than the benzylic carbon atom, thus attacking nitroolefin preferentially. In the context of the present invention, it was hypothesized that by modulating the relative nucleophilicities of the nitrogen and the carbon atoms of the hydrazone, a novel 1,3,4-selectivity might instead be achieved. In the literature, it has been shown that the reaction of nitroolefins with diazoalkanes, in which the carbon atom is more nucleophilic, affords 3,4-disubstituted pyrazoles ((a) Parham, W. E. et al. *J. Am. Chem. Soc.* 1950, 72, 3843-3846; (b) Mancera, M. et al. *J. Org. Chem.* 1988, 53, 5648-5651; (c) Aggarwal, V. K. et al. *J. Org. Chem.* 2003, 68, 5381-5383). In addition, 1,3,4-trisubstituted pyrazoles were obtained as minor products from the reaction of hydrazones with nitroolefins under microwave conditions (Arrieta, A. et al. *Tetrahedron* 1998, 54, 13167-1318).

Based on the limitations of literature methods and the prevalence of highly substituted pyrazole components in pharmaceutical agents, a general, convenient method in the synthesis of 1,3,4-substituted pyrazoles is highly desirable. Herein, we report a novel, regioselective synthesis of 1,3,4-trisubstituted and 1,3,4,5-tetrasubstituted pyrazoles from readily available hydrazones and nitroolefins under basic conditions. This reaction is quite general for a range of substrates, and has broad functional group compatibility.

SUMMARY OF THE INVENTION

In one aspect the invention relates to a process for the preparation of compounds of Formula (I) and salts thereof:

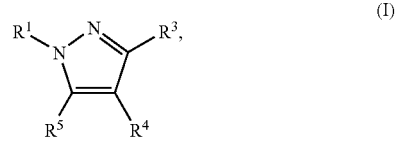

comprising
(a) reacting a hydrazone of formula (II):

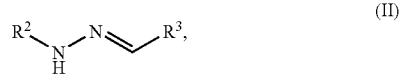

with a nitroolefin of formula (III):

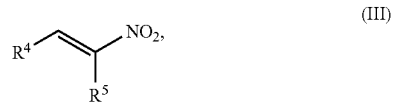

in the presence of a strong base, in a polar, aprotic organic solvent; and
(b) quenching the reaction with a strong acid;
wherein
$R^1$ is $C_{1-6}$alkyl, or an aryl group unsubstituted or substituted with one or two $R^a$ substituents;
  where each $R^a$ is independently —OH, —$OC_{1-6}$alkyl, —CN, —N($R^b$)$R^c$, —C(O)N($R^b$)$R^c$, —N($R^d$)C(O)$R^d$, —N($R^d$)$SO_2C_{1-6}$alkyl, —C(O)$C_{1-6}$alkyl, —S(O)$_{0-2}$—$C_{1-6}$alkyl, —$SO_2$N($R^b$)$R^c$, halo, —$CF_3$, —COOH, and —$COOC_{1-6}$alkyl;
    where $R^b$ and $R^c$ are each independently —H or —$C_{1-6}$alkyl; and
    where $R^d$ is —H or —$C_{1-6}$alkyl;
$R^3$ is —$CO_2C_{1-4}$alkyl, or an aryl or heteroaryl group unsubstituted or substituted with one or two $R^e$ substituents;
  where each $R^e$ is independently —OH, —$OC_{1-6}$alkyl, —CN, —N($R^f$)$R^g$, —C(O)N($R^f$)$R^g$, —N($R^h$)C(O)$R^h$, —N($R^h$)$SO_2C_{1-6}$alkyl, —C(O)$C_{1-6}$alkyl, —S(O)$_{0-2}$—$C_{1-6}$alkyl, —$SO_2$N($R^f$)$R^g$, halo, —$CF_3$, —COOH, and —$COOC_{1-6}$alkyl;
    where $R^f$ and $R^g$ are each independently —H or —$C_{1-6}$alkyl; and
    where $R^h$ is —H or —$C_{1-6}$alkyl;
$R^4$ is an aryl or heteroaryl group unsubstituted or substituted with one or two $R^i$ substituents;
  where each $R^i$ is independently —OH, —$OC_{1-6}$alkyl, —CN, —N($R^j$)$R^k$, —C(O)N($R^j$)$R^k$, —N($R^j$)C(O)$R^l$, —N($R^j$)$SO_2C_{1-6}$alkyl, —C(O)$C_{1-6}$alkyl, —S(O)$_{0-2}$—$C_{1-6}$alkyl, —$SO_2$N($R^j$)$R^k$, halo, —$CF_3$, —COOH, and —$COOC_{1-6}$alkyl;
    where $R^j$ and $R^k$ are each independently —H or —$C_{1-6}$alkyl; and where $R^1$ is —H or —$C_{1-6}$alkyl;

$R^5$ is H or methyl; or $R^4$ and $R^5$ together form —$(CH_2)_4$—; and the base is selected from the group consisting of potassium tert-butoxide, sodium tert-butoxide, lithium tert-butoxide, potassium isopropoxide, sodium isopropoxide, lithium isopropoxide, potassium bis(trimethylsilyl)amide, sodium bis(trimethylsilyl)amide, lithium bis(trimethylsilyl)amide, and isopropylmagnesium chloride.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by a bond "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

"Aryl", also "Ar" or "aryl", includes phenyl, also "Ph", and naphthyl.

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

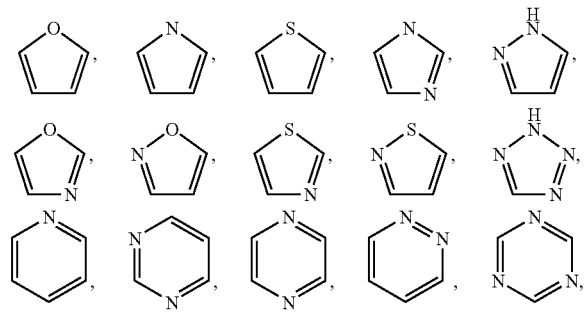

-continued

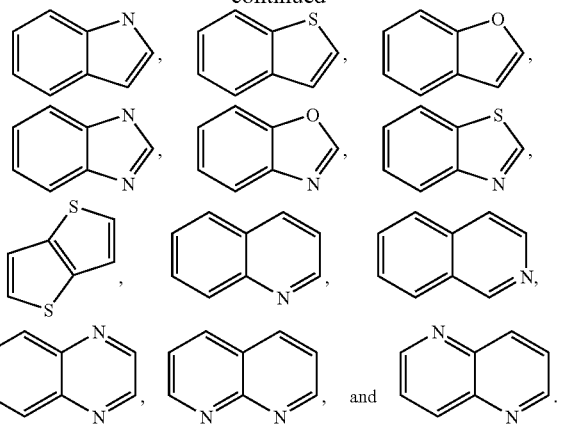

Those skilled in the art will recognize that the species of alkyl, aryl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "polar, aprotic organic solvent" refers to a solvent with a high dielectric constant (e.g. above 7.5), but which lacks hydroxyl groups or similar hydrogen-bond donating functionalities (Carey, F. A. and R. J. Sundberg, "Advanced Organic Chemistry," $3^{rd}$ ed., 1990, Part B, p. 21). Examples of polar, aprotic organic solvents include, but are not limited to, tetrahydrofuran, N,N-dimethylformamide, acetone, N,N-dimethylsulfoxide, N,N-dimethylacetamide, and acetonitrile.

The term "strong acid" as used herein represents a protic acid of a pH below about 4, including, but not limited to, TFA, methanesulfonic acid, benzenesulfonic acid, and para-toluenesulfonic acid (TsOH).

The ring positions of pyrazoles described herein, such as compounds of Formula (I), are numbered as follows:

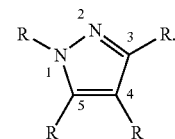

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In preferred embodiments of Formula (I), $R^1$ is phenyl, 4-cyanophenyl, 4-methoxyphenyl, 3,5-dichlorophenyl, naphthyl, or methyl.

In preferred embodiments, $R^3$ is phenyl, 4-chlorophenyl, 4-methoxycarbonylphenyl, 4-nitrophenyl, 3-cyanophenyl, 4-methoxyphenyl, 4-dimethylaminophenyl, or ethoxycarbonyl.

In preferred embodiments, $R^4$ is phenyl, benzo[1,3]dioxolyl, 2-chloro-6-fluorophenyl, 4-bromophenyl, 3-trifluoromethylphenyl, 4-nitrophenyl, 2-thienyl, 2-furanyl, or 3-pyridyl.

In preferred embodiments, $R^5$ is H.

In preferred embodiments, the strong base is KOtBu.

In preferred embodiments, the solvent is THF.

In preferred embodiments, the strong acid is TFA, methanesulfonic acid, benzenesulfonic acid, or para-toluenesulfonic acid. In further preferred embodiments, the strong acid is TFA.

A "salt" is intended to mean a salt of a free acid or base of a compound represented by Formula (I). A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

In the context of this invention, it seemed that a deprotonated hydrazone might possess a reversed nucleophilicity toward a Michael receptor such as a nitroolefin. Indeed, when potassium tert-butoxide (KOtBu or KOBu$^t$) was added to hydrazone 1 in tetrahydrofuran (THF) at 0° C. under $N_2$ followed by the addition of nitroolefin 2, 1,3,4-trisubstituted pyrazole 4 was isolated in 45% yield after 30 minutes at 0° C. (Scheme 2, reaction B). Although the yield was rather low, no 1,3,5-trisubstituted pyrazole 3 was observed. Notably, the base-mediated reaction B does not require air, which is essential for reaction A to proceed. Actually, when reaction B was performed in the presence of air, oxidative dimerization of the hydrazone itself was the dominant reaction (Buckingham, J. Q. Rev. Chem. Soc. 1969, 23, 37-56).

Scheme 2. Complementary regioselectivity in the reaction of hydrazone 1 with nitroolefin 2

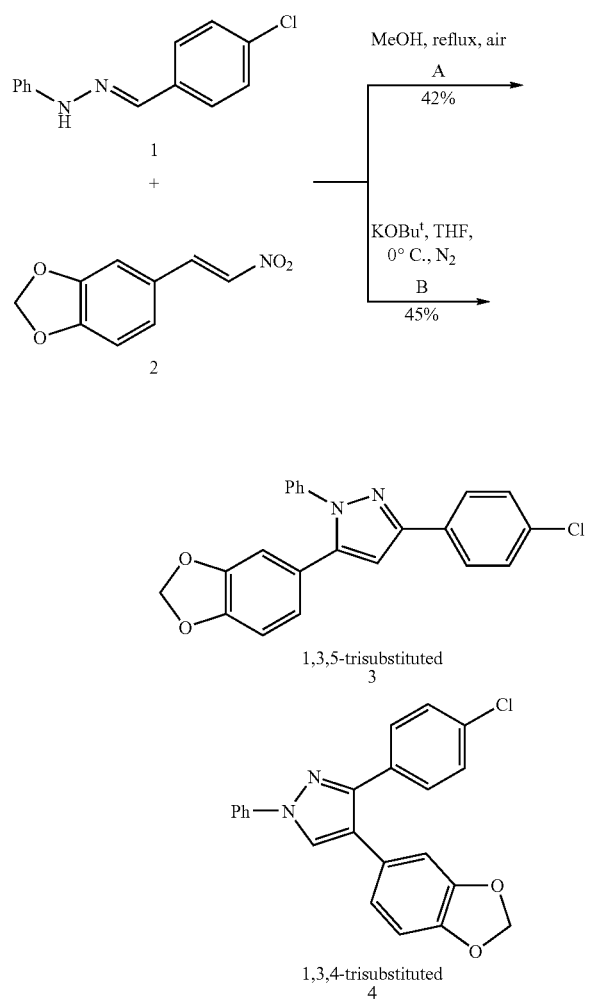

In attempts to optimize reaction B, altering the solvent (CH$_3$CN, CH$_2$Cl$_2$, N,N-dimethylformamide (DMF), N,N-dimethylacetamide (DMA)), reaction temperature (−78° C.), or strong base (NaOBu$^t$, LiOBu$^t$, sodium bis(trimethylsilyl)amide (NaHMDS), LiHMDS, and $^i$PrMgCl) all provided the desired pyrazole 4, most with comparable success to the KOBu$^t$/THF conditions. Using PhMgCl or lithium diisopropylamide (LDA) as the strong base afforded only trace amounts of product. Changing the order of addition of the reagents, by adding KOBu$^t$ to the solution of hydrazone 1 and nitroolefin 2 in THF, did not significantly affect the outcome.

Studies in the context of this invention revealed the outcome of the reaction depended on the quenching method used (Scheme 3). In these parallel experiments, KOBu$^t$ was added to −78° C. solutions of hydrazone 5 in THF under N$_2$, followed by the addition of nitroolefin 6 after 10 minutes. After stirring at −78° C. for a further 10 minutes, both hydrazone 5 and nitroolefin 6 were completely consumed based on HPLC analysis. Two equivalents of a quenching reagent selected from H$_2$O, MeOH, acetic acid (AcOH), benzenesulfonic acid, CH$_3$SO$_3$H, and TFA were then added to each reaction vessel. After further stirring at −78° C. for 2 hours, the reaction solutions were warmed to room temperature slowly overnight. The results are depicted in Scheme 3. When no quenching reagents or water were used, starting materials were mostly recovered. MeOH (pKa=15.5) quenching caused a very messy reaction. Besides the desired pyrazole 7 obtained in 12% yield, the only other isolable product was 5-aminopyrazole 8 in 18% yield, which perhaps arose from an internal Redox reaction. With AcOH (pKa=4.7) as the quenching reagent, desired pyrazole 7 was not observed. Instead, the major product was Michael addition product 9, isolated in 40% yield. Finally, when TFA (pKa=−0.25) was used as the quenching reagent, a clean transformation was achieved to afford desired pyrazole 7 in 77% isolated yield. Comparable isolated yields were also obtained with PhSO$_3$H (pKa=2.1) and CH$_3$SO$_3$H (pKa=−2.6) as the quenching reagents. It is important to note that when isolated compound 9 was subjected to the KOBu$^t$/TFA sequence, pyrazole 7 was obtained almost quantitatively, which suggests the intermediacy of compound 9 in the pyrazole forming reaction.

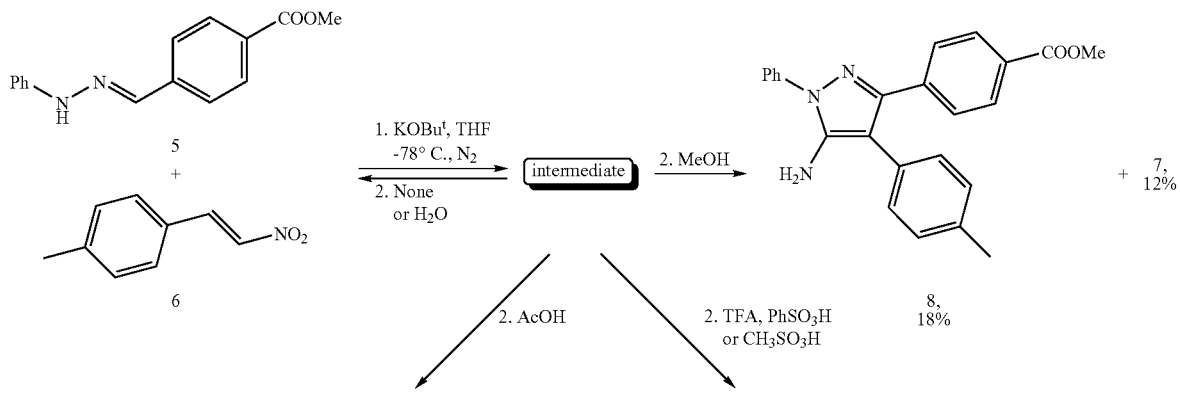

Scheme 3. Study of different quenching methods.

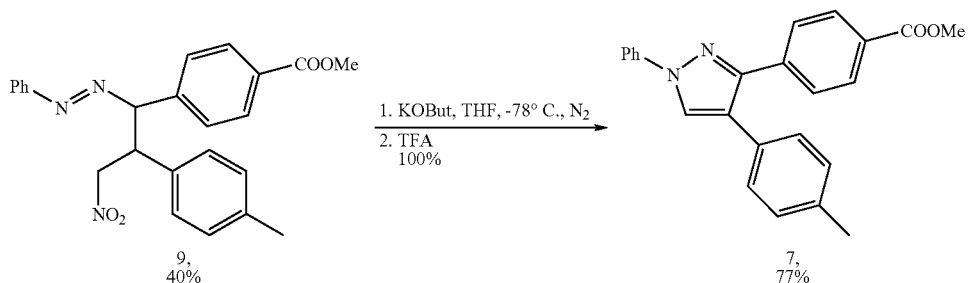

Without being bound by a particular hypothesis, a possible mechanism for the pyrazole formation reaction is shown in Scheme 4. Michael addition of deprotonated hydrazone 10 to a nitroolefin affords intermediate 11 ((a) Fernandez, R. et al. *Tetrahedron Lett.* 1994, 35, 471-472; (b) Enders, D. et al. *Synthesis* 1996, 48-52). An intramolecular addition then furnishes cyclized intermediate 12. An oxidative aromatization then generates the desired pyrazole product. Since the reaction is performed under $N_2$ without an external oxidant, the byproduct $HNO_2$ likely serves as an internal oxidant.

under basic conditions is a slow process, which allows other decomposition pathways to occur, resulting in the low yields observed with unquenched reactions. Conversely, strong acid protonation of intermediate 12 would afford intermediate 13, which perhaps allows a faster elimination of $HNO_2$, thus suppressing the other competing pathways.

With optimized conditions in hand and a reasonable understanding of the reaction mechanism, the scope of this reaction was examined (Table 1). A diverse set of representative nitroolefins was reacted with hydrazone 1 under the standard

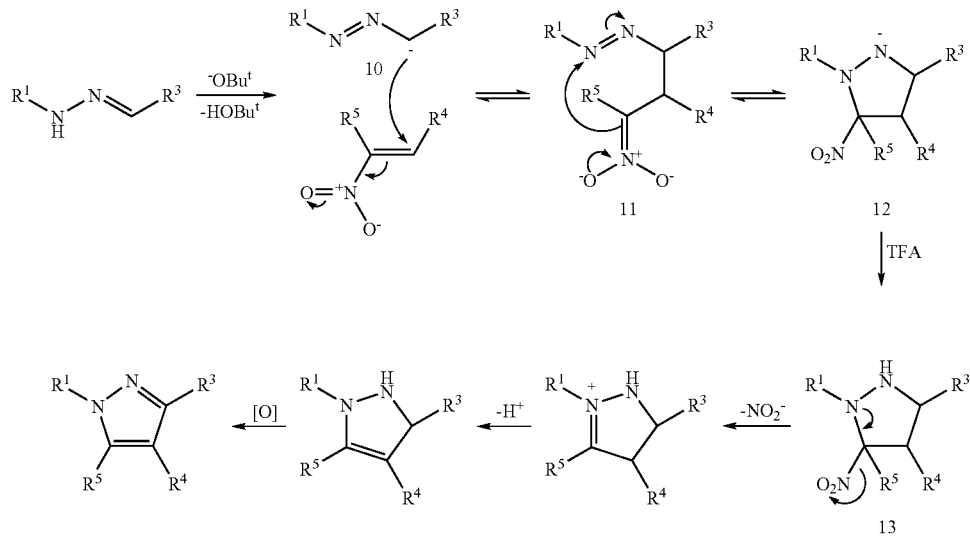

In this process, it is not clear whether intermediate 10 or 11 is the resting stage. Low temperature nuclear magnetic resonance (NMR) experiments (−25° C.) showed the disappearance of the starting materials in several minutes but failed to provide a clean spectrum of the proposed intermediate. Nevertheless, these first two steps are most likely reversible due to the fact that the starting materials are recovered when no quenching or water quenching is used. The role of a strong acid quenching agent in these reactions is not entirely clear. One possible explanation is that the elimination of $NO_2^-$ $KOBu^t$/TFA conditions without individual optimization. At the $R^4$ position, both electron-donating and electron-withdrawing groups, with various aromatic substitution patterns, are compatible with the reaction conditions (entries 1-5). Notably, a sterically hindered ortho-disubstituted nitroolefin worked efficiently (entry 2). Substitutions at the $R^5$ position were well tolerated (entries 6 and 7). Nitroolefins with aliphatic (entry 7) or heteroaryl groups such as thiophene, furan and pyridine (entries 8-10) at the $R^4$ position afforded good yields of pyrazoles as well.

TABLE 1
Reaction Scope with Respect to the Nitroolefin
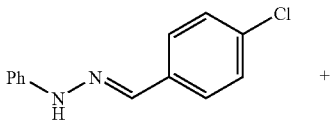
| entry | nitro-olefin | product | yield |
|---|---|---|---|
| 1 | 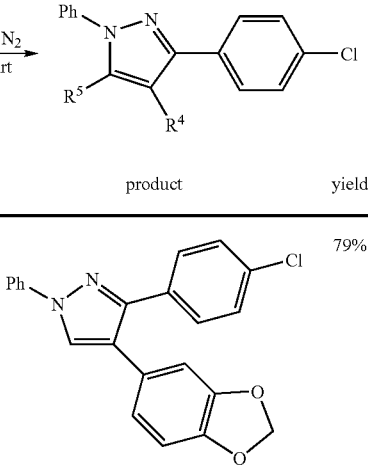 | 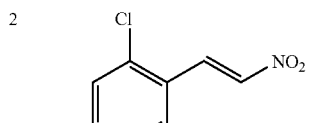 4 | 79% |
| 2 | 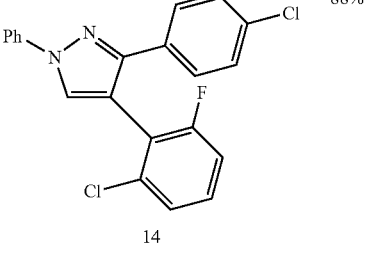 | 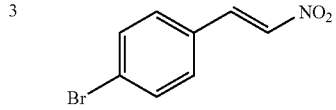 14 | 88% |
| 3 | 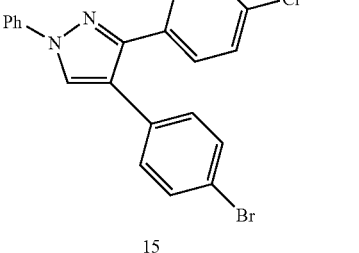 | 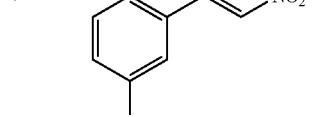 15 | 81% |
| 4 | 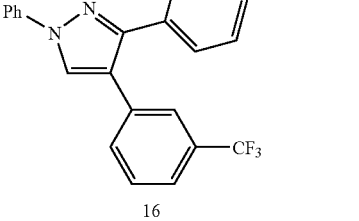 | 16 | 76% |

TABLE 1-continued
| | | | |
|---|---|---|---|
| 5 | 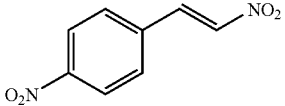 | 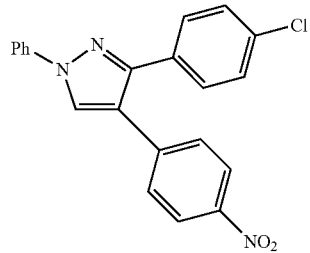  17 | 52% |
| 6 | 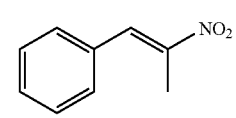 | 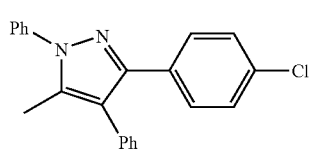  18 | 82% |
| 7 | 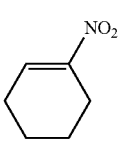 | 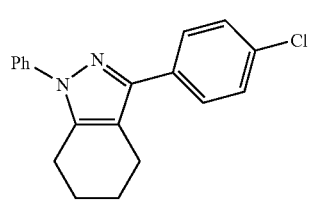  19 | 63% |
| 8 | 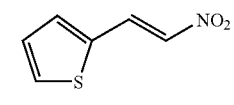 | 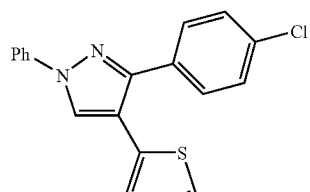  20 | 73% |
| 9 | 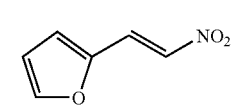 | 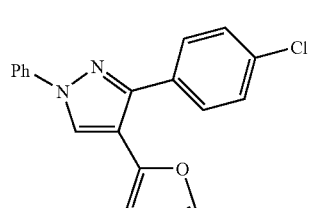  21 | 51% |
| 10 | 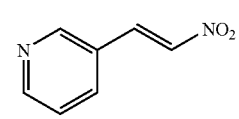 | 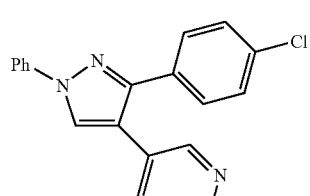  22 | 42% |

The scope of the reaction with respect to the hydrazone reagent was examined (Table 2). High yields were achieved when $R^3$ was a phenyl ring substituted with electron-withdrawing groups (Table 2, entries 1-3). With electron-donating substituents on the $R^3$ phenyl ring, products were observed, albeit in lower yield (entries 4-5). Without being bound by hypothesis, an electron-withdrawing group may help stabilize deprotonated hydrazone 10 (Scheme 4), thus facilitating the Michael addition step. Non-aromatic $R^3$ groups were also well tolerated, as pyrazole 32, the regioisomer of the key intermediate for rimonbant, was prepared in high yield (entry 10).

Substitution at the $R^1$ position was then investigated. Here the electronic effect was also prominent. However, the effect was observed in a reversed fashion: an electron-withdrawing substituent on an $R^1$ phenyl ring afforded a very poor yield (entry 6), whereas an electron-donating substituent facilitated the reaction (entry 7). Without being bound by hypothesis, the electronic properties of the $R^1$ group may have less of an effect on the first Michael addition step because the $R^1$ group is far away from the reaction site. Meanwhile, on the subsequent addition step, an electron-withdrawing $R^1$ group would significantly increase the electron-density on the adjacent nitrogen atom in intermediate 11, thus impeding the formation of intermediate 12. However, for pyridyl substituents at the $R^1$ position gave different results (entry 9). When no quenching was employed, desired pyrazole 31 was isolated in a low 16% yield (entry 9b). In contrast, with the strong acid quenching method, open-chain nitroso compound 30 was obtained in 81% yield (entry 9a), presumably through the dehydration of protonated intermediate 11. An electron-donating methyl group at the $R^1$ position was also compatible with the reaction conditions (entry 11). The relatively low yield was likely attributable to the instability of methylhydrazone itself. Compared with electronic properties, the steric properties of the $R^1$ substituent are less significant. A bulky naphthyl hydrazone furnished pyrazole 29 in 67% yield (entry 8).

TABLE 2

Reaction Scope with Respect to the Hydrazone

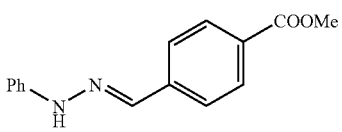

| entry | hydrazone | product | yield |
|---|---|---|---|
| 1 | 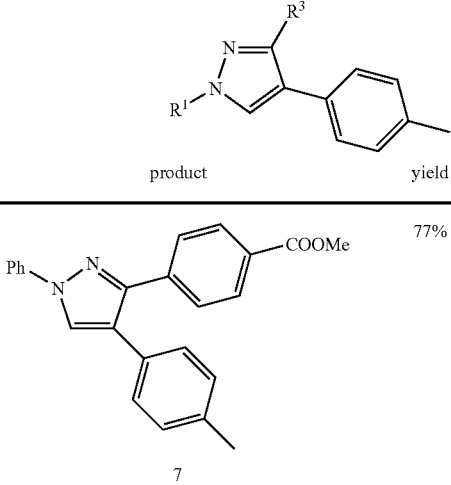 | | 77% |
| 2 | 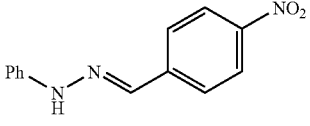 | 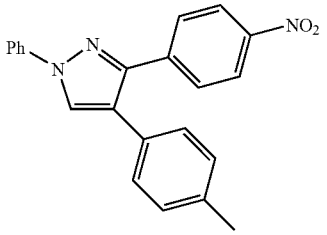 | 80% |

TABLE 2-continued
| | | | |
|---|---|---|---|
| 3 | 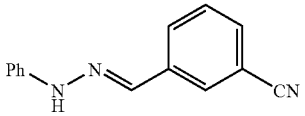 | 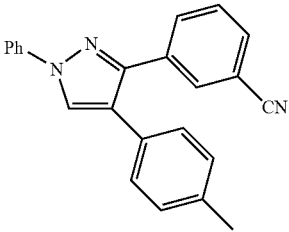 24 | 83% |
| 4 | 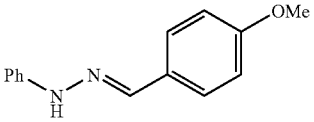 | 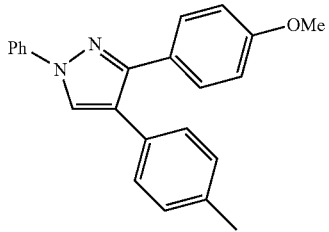 25 | 25% |
| 5 | 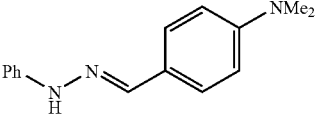 | 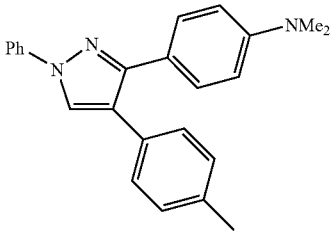 26 | 31% |
| 6 | 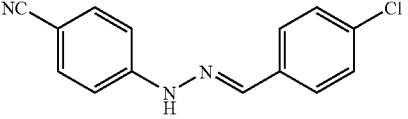 | 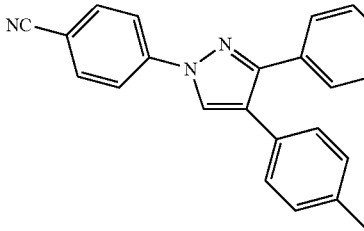 27 | 11% |
| 7 | 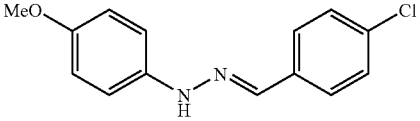 | 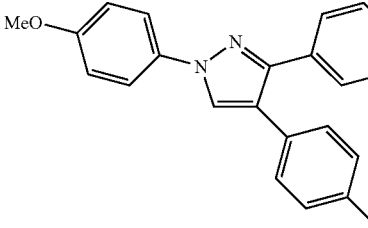 28 | 83% |

TABLE 2-continued

| | Starting material | | Product | Yield |
|---|---|---|---|---|
| 8 | (naphthyl-NH-N=CH-C6H4-Cl) | | 29 (1-naphthyl-3-(4-chlorophenyl)-4-(4-tolyl)pyrazole) | 67% |
| 9a | (2-pyridyl-NH-N=CH-C6H4-Cl) | | 30 (azo compound with nitroso group) | 81% |
| 9b[a] | (2-pyridyl-NH-N=CH-C6H4-Cl) | | 31 (1-(2-pyridyl)-3-(4-chlorophenyl)-4-(4-tolyl)pyrazole) | 16% |
| 10[b] | (2,4-dichlorophenyl-NH-N=CH-COOEt) | | 32 (1-(2,4-dichlorophenyl)-4-(4-chlorophenyl)-5-methyl-pyrazole-3-carboxylic acid ethyl ester) | 78% |
| 11 | (Me-NH-N=CH-C6H4-NO2) | | 33 (1-methyl-3-(4-nitrophenyl)-4-(4-tolyl)pyrazole) | 41% |

[a] This reaction was not quenched with TFA.

[b] 1-Chloro-4-(2-nitro-propenyl)-benzene was used in this reaction.

Compounds prepared according to the schemes described above may be isolated using conventional separation methods known to one skilled in the art, such as chromatography, crystallization, or salt formation.

Compounds of Formula (I) may be converted to their corresponding salts using methods known to those skilled in the art. For example, amines of Formula (I) may be treated with trifluoroacetic acid (TFA), HCl, maleic acid, or citric acid in a solvent such as diethyl ether ($Et_2O$), DCM, tetrahydrofuran (THF), or methanol (MeOH) to provide the corresponding salt forms.

Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

In conclusion, a regioselective synthesis of 1,3,4-trisubstituted or 1,3,4,5-tetrasubstituted pyrazoles from hydrazones and nitroolefins was developed. Under basic conditions, an unusual 1,3,4-regioselectivity pattern was obtained exclusively. A Michael addition product was postulated as a key intermediate and a plausible reaction mechanism was proposed. This reaction is quite broad in scope, generating a diverse set of pyrazole products in moderate to excellent yields. Partnered with the 1,3,5-trisubstituted pyrazole synthesis previously developed (Deng, X.; Mani, N. S. 2006), the reaction of hydrazones and nitroolefins provides a general method to access pyrazoles with different substitution patterns.

The following examples are provided to further illustrate the invention and various preferred embodiments.

EXAMPLES

Chemistry:

In preparing the compounds described in the examples below and obtaining the corresponding analytical data, the following experimental and analytical protocols were followed unless otherwise indicated.

Unless otherwise specified, reaction mixtures were magnetically stirred at room temperature (rt) under a $N_{2(g)}$ atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure.

The reaction flasks were flame-dried prior to use. THF was dried over alumina. All the hydrazones were prepared according from the corresponding aldehydes and hydrazines using methods known in the art. All the nitroolefins were purchased from commercial sources and used without further purification.

Normal phase flash column chromatography (FCC) was typically performed with Merck silica gel 60, unless otherwise indicated.

HPLC analysis was performed on a Hewlett Packard 1100, using an Agilent ZORBAX® Eclipse XDB-C8, 5 μm, 4.6× 150 mm column, a flow rate of 1 mL/min, and a gradient (acetonitrile/water with 0.05% trifluoroacetic acid) of 1% acetonitrile/99% water to 99% acetonitrile/1% water ramp over 8 min.

Nuclear magnetic resonance (NMR) spectra were obtained on Bruker model DRX spectrometers. The format of the $^1H$ NMR data below is: chemical shift in ppm downfield of the tetramethylsilane reference (multiplicity, coupling constant J in Hz, integration). Multiplicity is given as s (singlet), d (doublet), t (triplet), q (quartet), or m (multiplet). One-dimension Nuclear Overhauser Effect (NOE) experiments were performed at Bruker 500 NMR spectrometer by the method of Stott, et al. with a mixing time of 0.8 sec (Stott, K.; Keeler, J.; Van, Q. N.; Shaka, A. J. *J. Magn. Reson.*, 1997, 125, 302-324).

Infrared spectroscopy was performed on a Nicolet Avatar 360 FT-IR.

High resolution mass spectrometry (HRMS) was performed using electrospray ionization (ESI) on a Bruker μTof.

Chemical names were generated using ChemDraw Ultra 6.0.2 (CambridgeSoft Corp., Cambridge, Mass.).

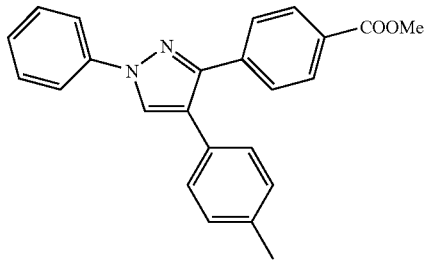

Example 1

4-(1-Phenyl-4-p-tolyl-1H-pyrazol-3-yl)-benzoic acid methyl ester

To a −78° C. solution of 4-(phenyl-hydrazonomethyl)-benzoic acid methyl ester (127 mg, 0.50 mmol, 1.0 equiv.) in THF (5 mL) was added KOBu$^t$ (1.0 mol/L in THF, 0.5 mL, 0.5 mmol, 1.0 equiv.) was added dropwise. After stirring at −78° C. for 10 min, trans-4-methyl-ω-nitrostyrene (82 mg, 0.5 mmol, 1.0 equiv.) in THF (2 mL) was added dropwise via syringe. After 15 min, TFA (77 uL, 1.0 mmol, 2.0 equiv) was added via syringe. The reaction solution was stirred at −78° C. for ca. 2 h and then allowed to warm to room temperature (rt) overnight. The solution was diluted with EtOAc (30 mL) and water (30 mL). The organic layer was separated, dried, and concentrated. The crude product was purified by FCC (EtOAc/hexanes) to afford the title compound in 77% yield (142 mg, 0.39 mmol). HPLC: $R_T$=11.78 min. TLC (EtOAc/Hexanes=1:4): $R_f$=0.35. $^1H$ NMR (500 MHz, CDCl$_3$, δ): 8.02-7.98 (m, 2H), 7.98 (s, 1H), 7.82-7.77 (m, 2H), 7.69 (dt, J=8.5, 1.8 Hz, 2H), 7.52-7.44 (m, 2H), 7.36-7.28 (m, 2H), 7.22 (dt, J=8.1, 1.6 Hz, 2H), 7.18-7.13 (m, 2H), 3.91 (s, 3H), 2.38 (s, 3H). $^{13}C$ NMR (125.7 MHz, CDCl$_3$, δ): 167.0, 149.2, 139.8, 137.8, 137.0, 129.6, 129.5, 129.3, 129.2, 128.6, 128.1, 126.8, 126.6, 123.4, 119.0, 52.0, 21.1. HRMS-ESI (m/z): [M+H]+ calcd for $C_{24}H_{21}N_2O_2$ 369.1598; found, 369.1592.

The compounds in Examples 2-24 were prepared using methods analogous to those described in Example 1, with exceptions where noted. Yields are provided in Tables 1 and 2.

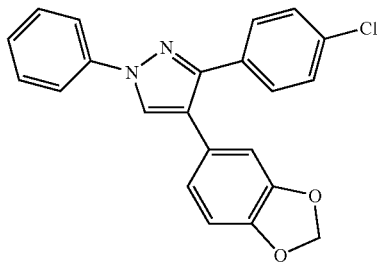

Example 2

4-Benzo[1,3]dioxol-5-yl-3-(4-chloro-phenyl)-1-phenyl-1H-pyrazole.

HPLC: $R_T$=11.65 min. TLC (EtOAc/Hexanes=1:4): $R_f$=0.33. 1H NMR (500 MHz, CDCl3, δ): 7.93 (s, 1H), 7.78-7.72 (m, 2H), 7.54 (td, J=8.6, 1.9 Hz, 2H), 7.50-7.42 (m, 2H), 7.34-7.27 (m, 3H), 6.81-6.79 (m, 2H), 6.79-6.76 (m, 1H), 5.98 (s, 2H). 13C NMR (125.7 MHz, CDCl3, δ): 149.13, 147.79, 146.86, 139.80, 133.79, 131.53, 129.58, 129.47, 128.54, 126.70, 126.57, 126.31, 122.68, 122.21, 118.92, 109.30, 108.54, 101.11. IR (dry film, cm$^{-1}$): 2907.1 (w), 1599.1 (m), 1502.1 (s), 1484.6 (s), 1439.5 (s), 1216.4 (s). HRMS-ESI (m/z): [M+H]+ calcd for $C_{22}H_{16}ClN_2O_2$ 375.0900; found, 375.0894.

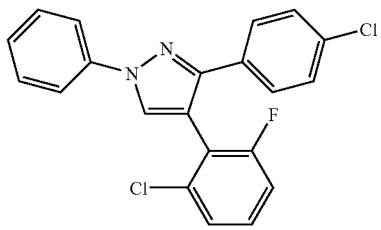

Example 3

4-(2-Chloro-6-fluoro-phenyl)-3-(4-chloro-phenyl)-1-phenyl-1H-pyrazole

HPLC: $R_T$=11.77 min. TLC (EtOAc/Hexanes=1:4): $R_f$=0.48. 1H NMR (500 MHz, CDCl3, δ): 8.01 (s, 1H), 7.79 (dt, J=8.2, 1.6 Hz, 2H), 7.52-7.44 (m, 4H), 7.34-7.22 (m, 5H), 7.08-7.02 (m, 1H). 13C NMR (125.7 MHz, CDCl3, δ): 171.1, 160.8 (d, $J_{C-F}$=249 Hz), 150.4, 139.8, 135.8, 133.9, 131.9, 129.8 (d, $J_{C-F}$=9.5 Hz), 129.5, 128.6, 128.1, 126.8, 125.5 (d, $J_{C-F}$=3.6 Hz), 120.8 (d, $J_{C-F}$=19.1 Hz), 119.1, 114.3 (d, $J_{C-F}$=22.9 Hz), 112.2. HRMS-ESI (m/z): [M+H]+ calcd for $C_{21}H_{14}N_2FCl_2$, 383.0513; found, 383.0519.

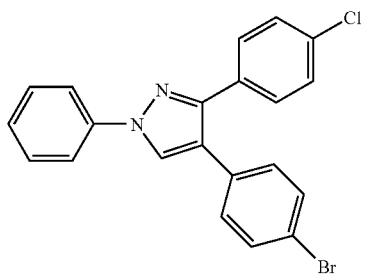

Example 4

4-(4-Bromo-phenyl)-3-(4-chloro-phenyl)-1-phenyl-1H-pyrazole

HPLC: $R_T$=12.75 min. TLC (EtOAc/Hexanes=1:4): $R_f$=0.47. 1H NMR (500 MHz, CDCl3, δ): 7.98 (s, 1H), 7.85-7.74 (m, 2H), 7.62-7.44 (m, 6H), 7.40-7.28 (m, 3H), 7.26-7.16 (m, 2H). 13C NMR (125.7 MHz, CDCl3, δ): 149.2, 139.7, 134.1, 131.8, 131.6, 131.3, 130.2, 129.7, 129.5, 128.7, 126.8, 126.7, 121.8, 121.2, 119.0. HRMS-ESI (m/z): [M+H]+ calcd for $C_{21}H_{15}N_2ClBr$, 409.0102; found, 409.0103.

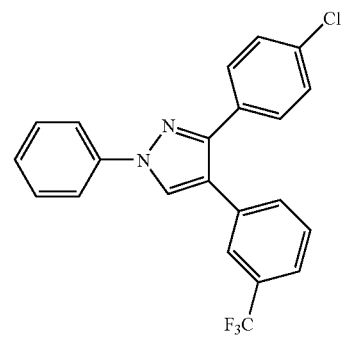

Example 5

3-(4-Chloro-phenyl)-1-phenyl-4-(3-trifluoromethyl-phenyl)-1H-pyrazole

HPLC: $R_T$=12.21 min. TLC (EtOAc/Hexanes=1:4): $R_f$=0.40. 1H NMR (500 MHz, CDCl3, δ): 8.03 (s, 1H), 7.84-7.76 (m, 2H), 7.63 (s, 1H), 7.60-7.40 (m, 7H), 7.38-7.26 (m, 3H). 13C NMR (125.7 MHz, CDCl3, δ): 149.3, 139.7, 134.2, 133.5, 132.0, 131.2, 131.1 (q, $J_{C-F}$=32.0 Hz), 129.7, 129.6, 129.1, 128.7, 127.1, 126.9, 125.2 (q, $J_{C-F}$=3.5 Hz), 123.8 (q, $J_{C-F}$=3.7 Hz), 124.0 (d, $J_{C-F}$=272 Hz), 121.5, 119.1. HRMS-ESI (m/z): [M+H]+ calcd for $C_{22}H_{15}N_2F_3Cl$, 399.0870; found, 399.0886.

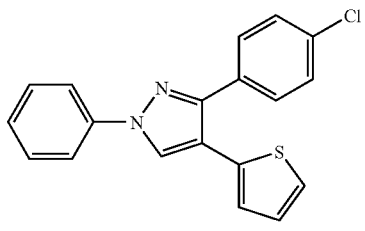

Example 6

3-(4-Chloro-phenyl)-4-(4-nitro-phenyl)-1-phenyl-1H-pyrazole

HPLC: $R_T$=11.02 min. TLC (EtOAc/Hexanes=1:4): $R_f$=0.23. $^1$H NMR (500 MHz, CDCl$_3$, δ): 8.20 (dt, J=8.8, 1.9 Hz, 2H), 8.12 (s, 1H), 7.82-7.76 (m, 2H), 7.57-7.45 (m, 6H), 7.41-7.34 (m, 3H). $^{13}$C NMR (125.7 MHz, CDCl$_3$, δ):149.7, 146.75, 139.6, 139.5, 134.6, 130.9, 129.9, 129.6, 128.9, 127.3, 127.2, 124.1, 120.9, 119.2. HRMS-ESI (m/z): [M+H]$^+$ calcd for C$_{21}$H$_{15}$N$_3$O$_2$Cl, 376.0847; found, 376.0849.

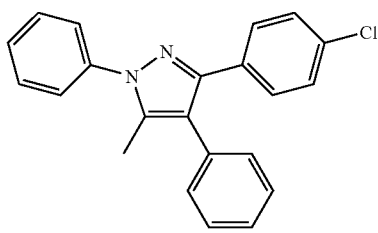

Example 7

3-(4-Chloro-phenyl)-5-methyl-1,4-diphenyl-1H-pyrazole

HPLC: $R_T$=11.84 min. TLC (EtOAc/Hexanes=1:4): $R_f$=0.39. $^1$H NMR (500 MHz, CDCl$_3$, δ): 7.60-7.55 (m, 2H), 7.51 (dt, J=7.5, 2.1 Hz, 2H), 7.46-7.36 (m, 5H), 7.32 (tt, J=7.3, 2.4 Hz, 2H), 7.28-7.24 (m, 2H), 7.22 (dt, J=8.7, 2.0 Hz, 2H), 2.30 (s, 3H). $^{13}$C NMR (125.7 MHz, CDCl$_3$, δ): 148.5, 139.9, 137.9, 133.6, 133.3, 131.9, 130.2, 129.3, 129.2, 128.6, 128.3, 127.9, 127.0, 125.1, 120.2, 11.6. HRMS-ESI (m/z): [M+H]$^+$ calcd for C$_{22}$H$_{18}$N$_2$Cl, 345.1153; found, 345.1155.

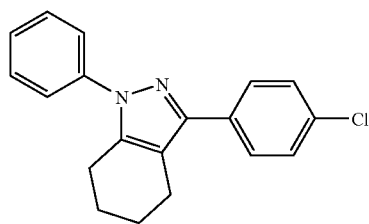

Example 8

3-(4-Chloro-phenyl)-1-phenyl-4,5,6,7-tetrahydro-1H-indazole

The analytical data obtained were identical with the literature data.

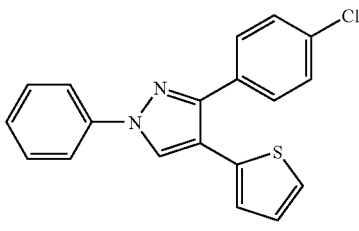

Example 9

3-(4-Chloro-phenyl)-1-phenyl-4-thiophen-2-yl-1H-pyrazole

HPLC: $R_T$=11.90 min. TLC (EtOAc/Hexanes=1:4): $R_f$=0.46. $^1$H NMR (500 MHz, CDCl$_3$, δ): 8.02 (s, 1H), 7.78-7.72 (m, 2H), 7.60 (dt, J=8.5, 1.8 Hz, 2H), 7.49-7.42 (m, 2H), 7.36-7.22 (m, 4H), 7.00 (dd, J=5.2, 3.5 Hz, 1H), 6.93 (dd, J=3.5, 1.1 Hz, 1H). $^{13}$C NMR (125.7 MHz, CDCl$_3$, δ): 149.4, 139.5, 134.1, 133.6, 131.2, 129.7, 129.4, 128.5, 127.5, 127.1, 126.7, 126.0, 124.9, 118.9, 115.8. HRMS-ESI (m/z): [M+H]$^+$ calcd for C$_{19}$H$_{14}$N$_2$SCl, 337.0561; found, 337.0568.

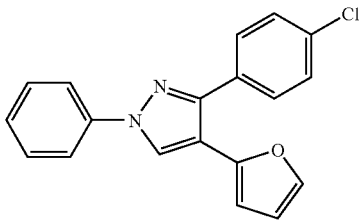

Example 10

3-(4-Chloro-phenyl)-4-furan-2-yl-1-phenyl-1H-pyrazole

HPLC: $R_T$=11.6 min. TLC (EtOAc/Hexanes=1:4): $R_f$=0.41. $^1$H NMR (500 MHz, CDCl$_3$, δ): 8.15 (s, 1H), 7.75 (dt, J=8.5, 2.0 Hz, 2H), 7.64 (dt, J=8.5, 1.9 Hz, 2H), 7.50-7.42 (m, 2H), 7.42, 7.36 (m, 3H), 7.33-7.27 (m, 1H), 6.39 (dd, J=3.3, 1.8 Hz, 1H), 6.24 (d, J=3.2 Hz, 1H). $^{13}$C NMR (125.7 MHz, CDCl$_3$, δ): 149.0, 146.9, 141.4, 139.6, 134.3, 131.6, 129.8, 129.5, 128.6, 126.8, 126.1, 119.0, 113.7, 111.2, 106.7. HRMS-ESI (m/z): [M+H]$^+$ calcd for C$_{19}$H$_{14}$N$_2$OCl, 321.0789; found, 321.0798.

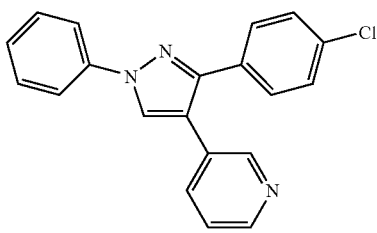

Example 11

3-[3-(4-Chloro-phenyl)-1-phenyl-1H-pyrazol-4-yl]-pyridine

The compound decomposed slowly during purification. HPLC: $R_T$=8.58 min. $^1$H NMR (500 MHz, CD$_3$OD, δ): 8.60 (s, 1H), 8.60-8.45 (m, 2H), 7.94-7.88 (m, 2H), 7.84-7.78 (m, 1H), 7.58-7.48 (m, 4H), 7.48-7.35 (m, 4H). $^{13}$C NMR (125.7 MHz, CD$_3$OD, δ): 150.9, 149.6, 148.5, 141.1, 138.1, 135.5, 132.8, 131.2, 130.7, 129.9, 129.6, 128.2, 120.3, 120.2. HRMS-ESI (m/z): [M+H]$^+$ calcd for C$_{20}$H$_{15}$ClN$_3$ 332.0949; found, 332.0949.

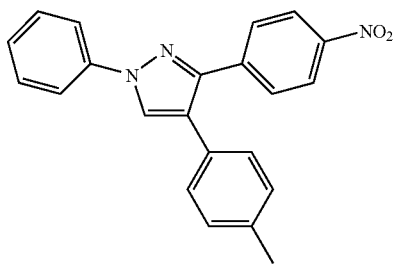

Example 12

3-(4-Nitro-phenyl)-1-phenyl-4-p-tolyl-1H-pyrazole

HPLC: $R_T$=11.71 min. TLC (EtOAc/Hexanes=1:4): $R_f$=0.34. $^1$H NMR (500 MHz, CDCl$_3$, δ): 8.15 (dt, J=8.9, 2.0 Hz, 2H), 7.99 (s, 1H), 7.82-7.77 (m, 4H), 7.52-7.46 (m, 2H), 7.33 (td, J=7.4, 1.0 Hz, 1H), 7.24-7.16 (m, 4H), 2.39 (s, 3H). $^{13}$C NMR (125.7 MHz, CDCl$_3$, δ): 147.7, 147.1, 139.8, 139.6, 137.3, 129.5, 129.5, 129.0, 128.7, 128.6, 127.2, 126.9, 123.7, 123.5, 119.0, 21.1. HRMS-ESI (m/z): [M+H]$^+$ calcd for C$_{22}$H$_{18}$N$_3$O$_2$ 356.1394; found, 356.1393.

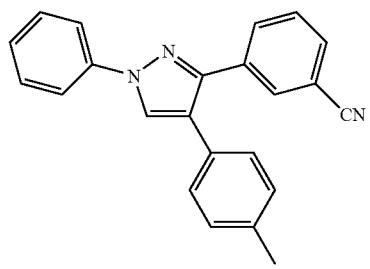

Example 13

3-(1-Phenyl-4-p-tolyl-1H-pyrazol-3-yl)-benzonitrile

HPLC: $R_T$=1.38 min. TLC (EtOAc/Hexanes=1:4): $R_f$=0.31. $^1$H NMR (500 MHz, CDCl$_3$, δ): 7.97 (s, 1H), 7.96 (t, J=1.3 Hz, 1H), 7.80 (dt, J=7.9, 1.3 Hz, 1H), 7.79-7.75 (m, 2H), 7.57 (dt, J=7.7, 1.3 Hz, 1H), 7.52-7.45 (m, 2H), 7.39 (t, J=7.8 Hz, 1H), 7.32 (tt, J=7.4, 1.0 Hz, 1H), 7.23-7.14 (m, 4H), 2.38 (s, 3H). $^{13}$C NMR (125.7 MHz, CDCl$_3$, δ): 147.8, 139.6, 137.2, 134.6, 132.4, 131.6, 131.1, 129.4, 129.4, 128.9, 128.5, 126.9, 126.7, 123.1, 118.9, 118.7, 112.4, 21.1. HRMS-ESI (m/z): [M+H]$^+$ calcd for C$_{23}$H$_{18}$N$_3$ 336.1495; found, 336.1497.

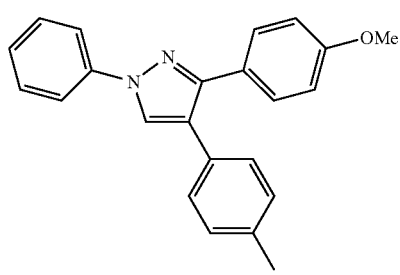

Example 14

3-(4-Methoxy-phenyl)-1-phenyl-4-p-tolyl-1H-pyrazole

HPLC: $R_T$=11.52 min. TLC (EtOAc/Hexanes=1:4): $R_f$=0.33. $^1$H NMR (400 MHz, CDCl$_3$, δ): 7.96 (s, 1H), 7.81-7.75 (m, 2H), 7.54 (dt, J=8.9, 2.1 Hz, 2H), 7.50-7.42 (m, 2H), 7.32-7.21 (m, 3H), 7.18-7.12 (m, 2H), 6.87 (dt, J=8.8, 2.1 Hz, 2H), 3.81 (s, 3H), 2.37 (s, 3H). $^{13}$C NMR (100 MHz, CDCl$_3$, δ): 159.3, 150.1, 139.9, 136.5, 129.9, 129.6, 129.3, 129.2, 128.5, 126.3, 126.1, 125.7, 122.5, 118.8, 113.7, 55.2, 21.1. HRMS-ESI (m/z): [M+H]$^+$ calcd for C$_{23}$H$_{21}$N$_2$O 341.1648; found, 341.1642.

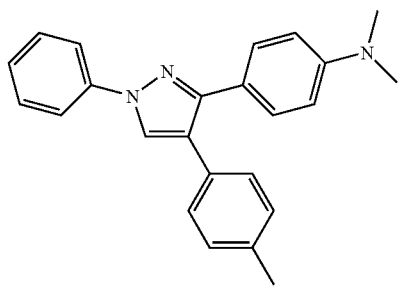

Example 15

Dimethyl-[4-(1-phenyl-4-p-tolyl-1H-pyrazol-3-yl)-phenyl]-amine

HPLC: $R_T$=9.69 min. TLC (EtOAc/Hexanes=1:4): $R_f$=0.35. $^1$H NMR (500 MHz, CDCl$_3$, δ): 7.94 (s, 1H), 7.81-7.75 (m, 2H), 7.60-7.40 (m, 4H), 7.32-7.22 (m, 3H), 7.18-7.12 (m, 2H), 6.73-6.67 (m, 2H), 2.96 (s, 6H), 2.37 (s, 3H). $^{13}$C NMR (125.7 MHz, CDCl$_3$, δ): 150.7, 150.0, 140.1, 136.3, 130.4, 129.3, 129.1, 129.1, 128.6, 126.3, 125.9, 122.3, 121.5, 118.7, 112.2, 40.5, 21.1. HRMS-ESI (m/z): [M+H]$^+$ calcd for C$_{24}$H$_{24}$N$_3$ 354.1965; found, 354.1973.

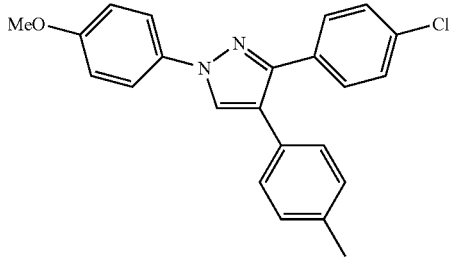

Example 16

3-(4-Chloro-phenyl)-1-(4-methoxy-phenyl)-4-p-tolyl-1H-pyrazole

HPLC: R$_T$=12.31 min. TLC (EtOAc/Hexanes=1:4): R$_f$=0.33. $^1$H NMR (500 MHz, CDCl$_3$, δ): 7.87 (s, 1H), 7.66 (dt, J=8.9, 1.9 Hz, 2H), 7.53 (dt, J=8.4, 2.3 Hz, 2H), 7.32-7.27 (m, 2H), 7.21 (d, J=7.9 Hz, 2H), 7.15 (d, J=7.9 Hz, 2H), 6.98 (dt, J=8.9, 1.9, 2H), 3.84 (s, 3H), 2.37 (s, 3H). $^{13}$C NMR (125.7 MHz, CDCl$_3$, δ): 158.3, 148.7, 136.7, 133.6, 133.5, 131.8, 129.6, 129.5, 129.3, 128.5, 128.4, 126.8, 122.4, 120.6, 114.5, 55.5, 21.1. HRMS-ESI (m/z): [M+H]$^+$ calcd for C$_{23}$H$_{20}$ClN$_2$O 375.1259; found, 375.1255.

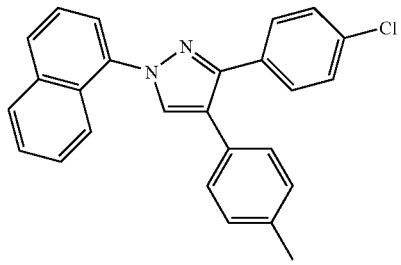

Example 17

3-(4-Chloro-phenyl)-1-naphthalen-1-yl-4-p-tolyl-1H-pyrazole

HPLC: R$_T$=12.69 min. TLC (EtOAc/Hexanes=1:4): R$_f$=0.43. $^1$H NMR (500 MHz, CDCl$_3$, δ): 8.08-8.02 (m, 1H), 7.96-7.88 (m, 2H), 7.84 (s, 1H), 7.64 (dd, J=7.3, 1.1 Hz, 1H), 7.59 (dt, J=8.6, 1.9 Hz, 2H), 7.57-7.52 (m, 3H), 7.33-7.26 (m, 4H), 7.17 (d, J=7.8 Hz, 2H), 2.38 (s, 3H). $^{13}$C NMR (125.7 MHz, CDCl$_3$, δ): 148.9, 137.0, 136.8, 134.4, 133.6, 131.82, 131.77, 129.72, 129.66, 129.4, 129.0, 128.9, 128.6, 128.5, 128.2, 127.3, 126.7, 125.1, 123.3, 123.1, 121.8, 21.2. HRMS-ESI (m/z): [M+H]$^+$ calcd for C$_{26}$H$_{20}$ClN$_2$ 395.1310; found, 395.1303.

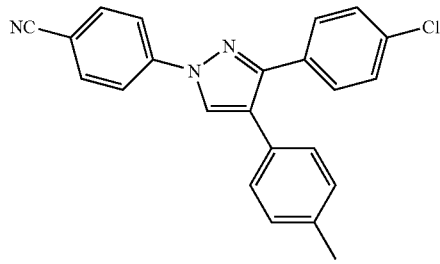

Example 18

4-[3-(4-Chloro-phenyl)-4-p-tolyl-pyrazol-1-yl]-benzonitrile

HPLC: R$_T$=12.08 min. TLC (EtOAc/Hexanes=1:4): R$_f$=0.25. $^1$H NMR (400 MHz, CDCl$_3$, δ): 8.03 (s, 1H), 7.91 (dt, J=8.9, 2.0 Hz, 2H), 7.77 (dt, J=8.9, 2.0 Hz, 2H), 7.53 (dt, J=8.6, 2.0 Hz, 2H), 7.31 (dt, J=8.6, 2.0 Hz, 2H), 7.24-7.15 (m, 4H), 2.39 (s, 3H). $^{13}$C NMR (100 MHz, CDCl$_3$, δ): 150.7, 142.6, 137.5, 134.3, 133.7, 131.0, 129.6, 129.5, 128.8, 128.64, 128.60, 126.46, 124.45, 118.6, 118.4, 109.6, 21.2. HRMS-ESI (m/z): [M+H]$^+$ calcd for C$_{23}$H$_{17}$ClN$_3$ 370.1106; found, 370.1098.

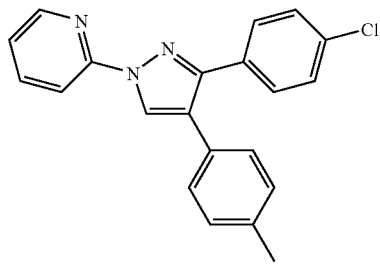

Example 19

2-[3-(4-Chloro-phenyl)-4-p-tolyl-pyrazol-1-yl]-pyridine

The solution of a mixture of N-(4-chloro-benzylidene)-N'-pyridin-2-yl-hydrazine (116 mg, 0.5 mmol, 1.0 equiv.) and trans-4-methyl-ω-nitrostyrene (82 mg, 0.5 mmol, 1.0 equiv.) in 7 mL THF was cooled to −78° C. Under N$^2$, KOBu$^t$ solution (1.0 mol/L, 0.5 mL, 0.5 mmol, 1.0 equiv.) was added dropwise via syringe. The reaction solution was stirred at −78° C. for ca. 2 hours and then allowed to warm to room temperature overnight. 30 mL EtOAc and 30 mL water were added. The organic layer was separated, dried over MgSO$_4$ and evaporated. The crude product was purified on column chromatography with EtOAc/hexanes as eluents to afford the title compound in 16% yield. HPLC: R$_T$=12.09 min. TLC (EtOAc/Hexanes=1:4): R$_f$=0.44. $^1$H NMR (500 MHz, CDCl$_3$, δ): 8.63 (s, 1H), 8.43 (d, J=4.1 Hz, 1H), 8.08 (d, J=8.3 Hz, 1H), 7.83 (ddd, J=8.3, 7.5, 1.8 Hz, 1H), 7.55 (dt, J=8.5, 1.9 Hz, 2H), 7.31 (dt, J=8.5, 1.9 Hz, 2H), 7.25-7.13 (m, 5H), 2.38 (s, 3H). $^{13}$C NMR (125.7 MHz, CDCl$_3$, δ): 151.3, 150.2, 148.0, 138.6, 136.9, 134.0, 131.7, 129.7, 129.5, 129.3, 128.6, 128.5, 126.8, 123.1, 121.4, 112.3, 21.2. HRMS-ESI (m/z): [M+H]$^+$ calcd for C$_{21}$H$_{17}$ClN$_3$ 346.1106; found, 346.1107.

33

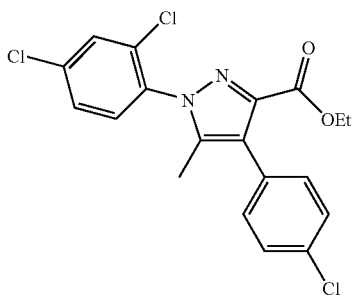

Example 20

4-(4-Chloro-phenyl)-1-(2,4-dichloro-phenyl)-5-methyl-1H-pyrazole-3-carboxylic acid ethyl ester HPLC: $R_T$=11.36 min. TLC (EtOAc/Hexanes=1:4): $R_f$=0.17. $^1$H NMR (500 MHz, CDCl$_3$, δ): 7.57 (d, J=2.0 Hz, 2H), 7.42 (s, 1H), 7.41 (d, J=2.0 Hz, 2H), 7.40-7.36 (m, 2H), 7.32-7.27 (m, 2H), 4.30 (q, J=7.12 Hz, 2H), 2.06 (s, 3H), 1.26 (t, J=7.12 Hz, 3H). $^{13}$C NMR (125.7 MHz, CDCl$_3$, δ): 162.14, 141.54, 140.40, 136.60, 135.27, 133.42, 133.24, 131.62, 130.55, 130.51, 130.19, 128.19, 128.10, 122.46, 61.01, 14.18, 10.25. IR (dry film, cm$^{-1}$): 1728.7 (s), 1489.8 (s), 1435.1 (w), 1180.5 (s), 1153.7 (s). HRMS-ESI (m/z): [M+H]$^+$ calcd for C$_{19}$H$_{16}$Cl$_3$N$_2$O$_2$ 409.0277; found, 409.0280.

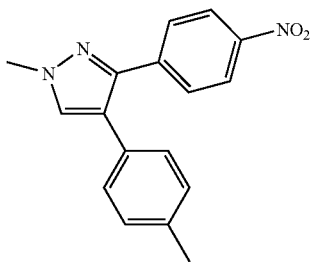

Example 21

1-Methyl-3-(4-nitro-phenyl)-4-p-tolyl-1H-pyrazole

HPLC: $R_T$=10.27 min. TLC (EtOAc/Hexanes=1:4): $R_f$=0.10. $^1$H NMR (500 MHz, CDCl$_3$, δ): 8.14 (dt, J=8.9, 2.0 Hz, 2H), 7.68 (dt, J=8.9, 2.0 Hz, 2H), 7.45 (s, 1H), 7.18-7.11 (m, 4H), 4.00 (s, 3H), 2.38 (s, 3H). $^{13}$C NMR (125.7 MHz, CDCl$_3$, δ): 146.9, 146.2, 140.3, 137.0, 130.8, 129.52, 129.47, 128.7, 128.4, 123.6, 122.1, 39.3, 21.2. The relative stereochemistry was confirmed by Noe study. HRMS-ESI (m/z): [M+H]$^+$ calcd for C$_{17}$H$_{16}$N$_3$O$_2$ 294.1237; found, 294.1227.

34

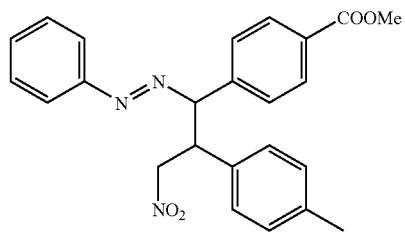

Example 22

4-(3-Nitro-1-phenylazo-2-p-tolyl-propyl)-benzoic acid methyl ester

Following the general method described above, AcOH instead of TFA was used to quench the reaction. After the same aqueous workup, 5 mL MeOH was added to the crude product and the solution was stirred at room temperature for 30 minutes. The yellow solid precipitated out was collected by filtration and washed with MeOH to afford the pure title compound in 40% yield. HPLC: $R_T$=10.65 min. $^1$H NMR (500 MHz, CDCl$_3$, δ): 8.02 (dt, J=8.4, 1.8 Hz, 2H), 7.62-7.55 (m, 2H), 7.48-7.40 (m, 5H), 7.05 (d, J=7.8 Hz, 2H), 7.02-6.96 (m, 2H), 5.07 (d, J=7.5, 1H), 4.73-4.62 (m, 2H), 4.44 (td, J=8.6, 6.5 Hz, 1H), 3.92 (s, 3H), 2.27 (s, 3H). $^{13}$C NMR (125.7 MHz, CDCl$_3$, δ): 166.6, 151.7, 142.5, 137.7, 132.25, 131.22, 130.1, 130.0, 129.4, 129.0, 128.6, 128.4, 122.5, 83.4, 52.22, 49.26, 21.07. A COSY NMR experiment confirmed that assigned structure. HRMS-ESI (m/z): [M+H]$^+$ calcd for C$_{24}$H$_{24}$N$_3$O$_4$ 418.1761; found, 418.1763.

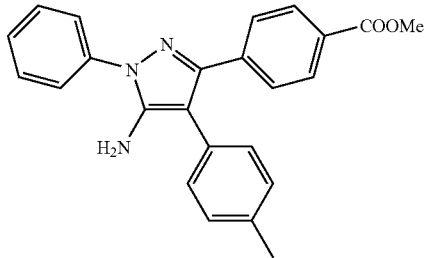

Example 23

4-(5-Amino-1-phenyl-4-p-tolyl-1H-pyrazol-3-yl)-benzoic acid methyl ester

Following the general method described above, MeOH instead of TFA was used to quench the reaction. After the same aqueous workup and purification procedure, in addition to the desired product (ca. 13% yield), the title compound isolated in 18% yield. HPLC: $R_T$=10.15min. TLC (EtOAc/Hexanes=1:4): $R_f$=0.14. $^1$H NMR (500 MHz, DMSO-d6, δ): 7.86 (dt, J=8.5, 1.8 Hz, 2H), 7.74-7.70 (m, 2H), 7.58-7.50 (m, 4H), 7.40 (tt, J=7.4, 1.0 Hz, 1H), 7.20 (d, J=7.8 Hz, 2H), 7.11 (d, J=8.0 Hz, 2H), 5.08 (s, 2H), 3.83 (s, 3H), 2.33 (s, 3H). $^{13}$C NMR (125.7 MHz, DMSO-d6, δ): 165.9, 147.0, 144.7, 138.8, 138.4, 135.4, 129.6, 129.5, 129.3, 129.2, 128.9, 128.2, 127.4, 126.9, 123.4, 103.4, 51.9, 20.7. Noe and COSY experiments were used to confirm the assigned structure. HRMS-ESI (m/z): [M+H]$^+$ calcd for C$_{24}$H$_{22}$N$_3$O$_2$ 384.1707; found, 384.1703.

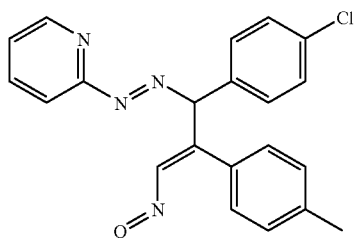

Example 24

[1-(4-Chloro-phenyl)-3-nitroso-2-p-tolyl-allyl]-pyridin-2-yl-diazene

Following the general method described above, after aqueous workup with EtOAc/water (even brine caused the decomposition of the title compound), the crude product was directly purified on prep. HPLC to afford the title compound in 81% yield. Based on NMR spectra, two inseparable isomers with identical MS existed, presumably from the cis-trans isomers. HPLC: $R_T$=8.71 min. $^1$H NMR (500 MHz, DMSO-d6, δ): 12.36 (s, 1H), 8.7 (dt, J=6.6, 1.0 Hz, 1H), 8.43 (ddd, J=8.9, 7.2, 1.3 Hz, 1H), 8.10 (s, 1H), 8.07-7.98 (m, 1H), 7.74 (dt, J=8.6, 1.8 Hz, 2H), 7.59 (d, J=8.2 Hz, 2H), 7.53 (dt, J=8.5, 1.7 Hz, 2H), 7.39 (td, J=7.1, 1.0 Hz, 1H), 7.21 (d, J=8.0 Hz, 2H), 6.85 (s, 1H), 2.28 (s, 3H). $^{13}$C NMR (125.7 MHz, DMSO-d6, δ): 152.1, 148.5, 147.2, 147.0, 139.6, 136.2, 131.9, 130.0, 129.8, 129.66, 129.59, 129.0, 127.6, 117.8, 111.1, 61.5, 21.2. HRMS-ESI (m/z): [M+H]$^+$ calcd for $C_{21}H_{18}ClN_4O$ 377.1164; found, 377.1167.

What is claimed is:

1. A process for the preparation of compounds of Formula (I) and salts thereof:

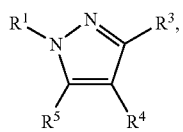

comprising (a) reacting a hydrazone of formula (II):

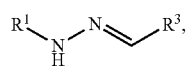

with a nitroolefin of formula (III):

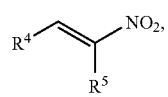

in the presence of a strong base of formula (XI):

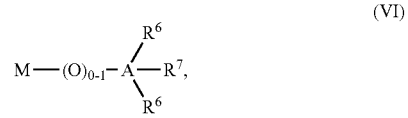

in a polar, aprotic organic solvent; and (b) quenching the reaction with a strong acid; wherein $R^1$ is $C_{1-6}$alkyl, or an aryl group unsubstituted or substituted with one or two $R^a$ substituents;
where each $R^a$ is independently —OH, —OC$_{1-6}$alkyl, —CN, —N(R$^b$)R$^c$, —C(O)N(R$^b$)R$^c$, —N(R$^d$)C(O)R$^d$, —N(R$^d$)SO$_2$C$_{1-6}$alkyl, —C(O)C$_{1-6}$alkyl, —S(O)$_{0-2}$—C$_{1-6}$alkyl, —SO$_2$N(R$^b$)R$^c$, halo, —CF$_3$, —COOH, and —COOC$_{1-6}$alkyl;
where R$^b$ and R$^c$ are each independently —H or —C$_{1-6}$alkyl; and
where R$^d$ is —H or —C$_{1-6}$alkyl;

$R^3$ is —CO$_2$C$_{1-4}$alkyl, or an aryl or heteroaryl group unsubstituted or substituted with one or two R$^e$ substituents;
where each R$^e$ is independently —OH, —OC$_{1-6}$alkyl, —CN, —N(R$^f$)R$^g$, —C(O)N(R$^f$)R$^g$, —N(R$^h$)C(O)R$^h$, —N(R$^h$)SO$_2$C$_{1-6}$alkyl, —C(O)C$_{1-6}$alkyl, —S(O)$_{0-2}$—C$_{1-6}$alkyl, —SO$_2$N(R$^f$)R$^g$, halo, —CF$_3$, —COOH, and —COOC$_{1-6}$alkyl;
where R$^f$ and R$^g$ are each independently —H or —C$_{1-6}$alkyl; and
where R$^h$ is —H or —C$_{1-6}$alkyl;

$R^4$ is an aryl or heteroaryl group unsubstituted or substituted with one or two R$^i$ substituents;
where each R$^i$ is independently —OH, —OC$_{1-6}$alkyl, —CN, —N(R$^j$)R$^k$, —C(O)N(R$^j$)R$^k$, —N(R$^l$)C(O)R$^l$, —N(R$^l$)SO$_2$C$_{1-6}$alkyl, —C(O)C$_{1-6}$alkyl, —S(O)$_{0-2}$—C$_{1-6}$alkyl, —SO$_2$N(R$^j$)R$^k$, halo, —CF$_3$, —COOH, and —COOC$_{1-6}$alkyl;
where R$^j$ and R$^k$ are each independently —H or —C$_{1-6}$alkyl; and
where R$^l$ is —H or —C$_{1-6}$alkyl;

$R^5$ is H or methyl; or $R^4$ and $R^5$ together form —(CH$_2$)$_4$—;
M is lithium, sodium, or potassium,
A is carbon or silicon;
each $R^6$ is independently $C_{1-4}$alkyl; and
$R^7$ is H or $C_{1-4}$alkyl.

2. The process according to claim 1, wherein $R^1$ is phenyl, 4-cyanophenyl, 4-methoxyphenyl, 3,5-dichlorophenyl, naphthyl, or methyl.

3. The process according to claim 1, wherein $R^3$ is phenyl, 4-chlorophenyl, 4-methoxycarbonylphenyl, 4-nitrophenyl, 3-cyanophenyl, 4-methoxyphenyl, 4-dimethylaminophenyl, or ethoxycarbonyl.

4. The process according to claim 1, wherein $R^4$ is phenyl, benzo[1,3]dioxolyl, 2-chloro-6-fluorophenyl, 4-bromophenyl, 3-trifluoromethylphenyl, 4-nitrophenyl, 2-thienyl, 2-furanyl, or 3-pyridyl.

5. The process according to claim 1, wherein $R^5$ is H.

6. The process according to claim 1, wherein strong base of formula (VI) is KOtBu.

7. The process according to claim 1, wherein the solvent is THF.

8. The process according to claim 1, wherein the strong acid is TFA, methanesulfonic acid, benzenesulfonic acid, or para-toluenesulfonic acid.

9. The process according to claim 1, wherein the strong acid is TFA.

* * * * *